(12) United States Patent
Zheng et al.

(10) Patent No.: US 9,115,377 B2
(45) Date of Patent: Aug. 25, 2015

(54) ***AMYCOLATOPSIS* SP. STRAIN AND METHODS OF USING THE SAME FOR VANILLIN PRODUCTION**

(75) Inventors: Pu Zheng, Wuxi (CN); Hui Li, Wuxi (CN); Xinglin Wang, Wuxi (CN); Jianhai Zhou, Wuxi (CN); Shibiao Chu, Wuxi (CN)

(73) Assignee: BGN Tech LLC, Rancho Santa Margarita, CA (US)

(*) Notice: Subject to any disclaimer, the term of this patent is extended or adjusted under 35 U.S.C. 154(b) by 241 days.

(21) Appl. No.: 13/591,231

(22) Filed: Aug. 22, 2012

(65) Prior Publication Data

US 2013/0115667 A1    May 9, 2013

(30) Foreign Application Priority Data

Oct. 24, 2011    (CN) .......................... 2011 1 0325488

(51) Int. Cl.
*C12N 1/20* (2006.01)
*C07C 47/58* (2006.01)
*C12P 7/24* (2006.01)
*C12R 1/01* (2006.01)
*A61K 38/00* (2006.01)

(52) U.S. Cl.
CPC ... *C12P 7/24* (2013.01); *C12N 1/20* (2013.01); *C12R 1/01* (2013.01)

(58) Field of Classification Search
CPC ....................................................... C12N 1/20
See application file for complete search history.

(56) References Cited

U.S. PATENT DOCUMENTS

| | | | | |
|---|---|---|---|---|
| 4,183,807 A * | 1/1980 | Yoshizawa et al. | ........... | 210/611 |
| 5,164,310 A * | 11/1992 | Smith et al. | ................... | 800/294 |
| 5,294,615 A * | 3/1994 | Meyer et al. | ............. | 514/252.17 |
| 5,646,030 A * | 7/1997 | Ray et al. | ..................... | 435/6.15 |
| 6,235,507 B1 * | 5/2001 | Muheim et al. | ............... | 435/147 |
| 7,157,080 B2 * | 1/2007 | Radice et al. | ................ | 424/93.7 |
| 7,462,470 B2 * | 12/2008 | Sun et al. | ........................ | 435/146 |
| 2004/0077848 A1 * | 4/2004 | Oreste et al. | .................... | 536/54 |
| 2007/0270620 A1 * | 11/2007 | Borthakur | ..................... | 568/438 |
| 2011/0136177 A1 * | 6/2011 | Hansen et al. | .................. | 435/73 |
| 2014/0249144 A1 * | 9/2014 | Ashikawa et al. | ......... | 514/232.5 |

OTHER PUBLICATIONS

Lohninger H. (2011) "Sodium Sulfate", pp. 1-2.*
Bian et al. (2009) *Amycolatopsis marina* sp. nov., an actinomycete isolated from an ocean sediment, Internat. J. System. Evolut. Microbiol., vol. 59, pp. 477-481.*
Davis et al. (2012)Genome Sequence of *Amycolatopsis* sp. Strain ATCC 39116, a Plant Biomass-Degrading Actinomycete, J. Bacteriol., vol. 194, pp. 2396-2397.*
Torres et al. (2009) Vanillin bioproduction from alkaline hydrolyzate of corn cob by *Escherichia coli* JM109/pBB1, Enyme Microb. Technol., vol. 44, pp. 154-158.*
Nakamura et al. (2001) Purification and characterization of an extracellular poly(L-lactic acid) depolymerase from a soil isolate, *Amycolatopsis* sp. strain K104-1, Appl. Enviorn. Microbiol., vol. 67, No. 1, pp. 345-353.*

* cited by examiner

*Primary Examiner* — Manjunath Rao
*Assistant Examiner* — Samuel Liu
(74) *Attorney, Agent, or Firm* — Nixon Peabody LLP; David S. Resnick; Candace M. Summerford

(57) ABSTRACT

This invention provides an *Amycolatopsis* sp. strain (zhp06), and a method of using the whole cell preparation of the strain for vanillin production. The strain was deposited in China Center for Type Culture Collection on Jul. 26, 2011 with the number of CCTCC NO: M 2011265. Under high concentrations of ferulic acid substrate, the vanillin production by this method can reach more than 10 g/L. The molar conversion rate of ferulic acid is more than 50% and the purity of vanillin is from 80% to 95%. The advantage of this invention includes: repeated use of biocatalyst cells, mild biotransformation condition, low environmental pollution, short production cycle, high product purity and simple purification procedure. It has a great potential for industrial applications.

9 Claims, No Drawings

AMYCOLATOPSIS SP. STRAIN AND METHODS OF USING THE SAME FOR VANILLIN PRODUCTION

CROSS-REFERENCE TO RELATED APPLICATIONS

This application claims the benefit of Chinese patent application No. 201110325488.1, filed Oct. 24, 2011, the contents of which are incorporated by reference herein.

BACKGROUND OF THE INVENTION

1. Field of the Invention

This invention is in the field of biotechnology, and in particular, it relates to a new *Amycolatopsis* sp. Strain (zhp6), and methods for using the new strain to produce vanillin from ferulic acid.

2. Description of the Related Art

Vanillin (chemical name: 3-methoxy-4-hydroxybenzaldehyde) has a molecular weight of 152.1. Vanillin appears as white to slightly yellow needle-like crystal or crystal powder. It is the primary component of the extract of vanilla seed pods. Vanillin exists in natural plants in free or glucoside forms. It accounts for 1.5% to 3% of the dry weight of vanilla beans, and is the major component among more than 200 flavors found in vanilla. Due to its creamy sweet flavor and aroma, vanillin is widely used as a flavor compound in ice cream, chocolate and dairy desserts and other food products, and is called the world's most widely used flavor enhancer.

In today's market, most vanillin is chemically synthesized from guaiacol (annual production of 12000 tons, $16/kg), and only very small portion of vanillin is naturally extracted from *vanilla planifolia* (annual production of 20 tons, $3200/kg). Although chemical synthesis to produce vanillin is a mature technology, the method brings serious environmental pollution. The security of chemical production of vanillin began to be questioned. Another disadvantage of chemical method is that it produces a product with only single aroma. Due to the high production cost and high consumption price, naturally extracted vanillin cannot meet people's demand for consumption. This promotes the development of bio-transformation technologies for vanillin production. In recent years, it has become a current trend to produce bio-vanillin from precursor substrates using microbial cells (Current Opinion in Biotechnology 2000, 11:490-496).

Ferulic acid is a precursor substrate of vanillin production. Depending on types of micro-organisms, there are one-step and two-step microbial transformation methods for vanillin production. Chinese Patent Nos. CN1421523A and CN 1824783A disclosed a two-step method that ferulic acid is first converted to vanillic acid, and vanillic acid is converted to vanillin using *Aspergillus niger* CGMCC 0774 and *Pycnoporuscinnabarinus* CGMCC 1115. This method requires the usage of two microbial organisms and is very time consuming.

U.S. Pat. No. 6,133,003 disclosed a one-step method for converting ferulic acid to vanillin using *Amycolatopsis* DSM 9991 and DSM 9992 strains. After microbial cells grew in the fermenter for 12.5 hours, ferulic acid was added to fermentation broth at different stages. Fermentation continued for another 50 hours until vanillin in fermentation broth reached 11.5 g/L with a converting rate of 77.8%. U.S. Pat. No. 6,235,507 disclosed a one-step method using *Streptomyces setonni* ATCC 39116. Microorganisms were inoculated in the growth medium and grew for 20-40 hours. When glucose in the growth medium was consumed, ferulic acid substrate was added to the fermentation broth at different phases. Fermentation was continued for another 5-50 hours. The fermentation broth can accumulate 8-16 g/L of vanillin and by-products such as vanillic alcohol, vanillic acid, guaiacol, vinyl guaiacol and 2-methoxy-4-ethyl phenol. Organic solvents such as methyl butyl ether (MTBE) was used to adjust pH and separate vanillin from the by-products. The yield of vanillin and the conversion rate in the above-mentioned inventions is relatively high, but the timing of adding ferulic acid substrate is hard to control, the microorganism strain is difficult to obtain, and there are many byproducts generated by these methods. Another method by Qingli Zhou used *Streptomyces* sp. L1936 strain for converting ferulic acid to vanillin. This method needs to add ferulic acid two times to the fermentation broth. The yield of vanillin was 7.12 g/L and the molar conversion rate was 69.9% (Food and Fermentation Industries, 2004, 30 (3): 18-20).

Chinese patent No. CN 101165168A disclosed a fermentation method using *Streptomyces* sp.V-1 (CCTCC M 206065) strain for generating vanillin from ferulic acid. This method used CY growth medium for growing microorganisms and DM11 macroporous absorbent resin for vanillin purification. Ferulic acid was added to the fermentation broth at different stages until the final concentration reached 45 g/L. The final yield of vanillin was 19.2 g/L and the molar conversion rate was 54.5%. The disadvantage of these two methods is that they both need to add ferulic acid for multiple times, which makes the operational control difficult.

SUMMARY OF THE INVENTION

This invention provides an *Amycolatopsis* sp. strain (zhp06) and methods for converting ferulic acid to vanillin using the *Amycolatopsis* sp. strain.

This invention provides an *Amycolatopsis* sp. strain (zhp06), which was deposited in China Center for Type Culture Collection on Jul. 26, 2011 with the number of CCTCC NO: M 2011265. The characteristic of this strain is as follows. The body of the bacteria is filamentous, the colony color is *incanus* or yellow, and the spore appears ellipsoid. The optimal temperature for growth is from 28° C. to 37° C. with the ability to grow at 50-55° C. Its 16S rRNA sequence shares 98-99% homology with those of many known *Amycolatopsis* sp. strains.

This invention provides a method of converting ferulic acid to vanillin using strain *Amycolatopsis* sp. zhp06, comprising the following steps:

1. *Amycolatopsis* sp. zhp06 cells or mutant strains were cultivated using a standard culture process. The cultured cells were collected by centrifugation.

2. The cells obtained from step 1 were added to a substrate solution to form a biotransformation solution. The cells were used as a biocatalyst to convert ferulic acid to vanillin during the biotransformation reaction.

3. Vanillin was extracted from the above biotransformation solution using macroporous absorbent resins.

In step one, the fermentation medium contains glucose 5-15 g/L, yeast extract 1-20 g/L, $Na_2HPO_4 \cdot 10H_2O$ 1-10 g/L, $KH_2PO_4$ 0.1-2 g/L, NaCl 0.1-0.5 g/L, $MgSO_4 \cdot 7H_2O$ 0.2-0.5 g/L, $CaCl_2 \cdot 2H_2O$ 0.01-0.1 g/L, ferulic acid 0.05-0.5 g/L, pH 7.2-7.4. The above medium is sterilized at 121° C. for 20 min.

In step two, the ratio of wet weight of zhp 06 cells (g) and the volume of the ferulic acid solution (ml) is from 1:2 to 1:20. The substrate solution contains ferulic acid 3-40 g/L, $Na_2HPO_4 \cdot 10H_2O$ 1-10 g/L and $KH_2PO_4$ 0.1-0.5 g/L (pH 7.5-7.9). The biotransformation reaction was performed at 28-45° C. for 20-70 hours.

After 5-12 hours of biotransformation reaction in step 2, 5-10% (w/v, g/ml) macroporous resin HZ-16 or HZ-802 (Shanghai Huazhen Science and Technology Inc., Shanghai, China) was added to the biotransformation solution. When the extracting reaction was over, the macroporous resin was filtered out and eluted with acetic ether or alcohol (2 times of the resin volume) at 35-40° C. The eluted solution was dried by anhydrous sodium sulfate for 12-15 hours and was filtered to remove sodium sulfate. The filtered solution was concentrated to achieve 200-230 g/L vanillin under vacuum evaporation. The concentrated solution was then left at 4° C. for vanillin crystallization.

The carbon source in fermentation medium is selected form glucose, starch, sucrose, fructose and maltose.

DETAILED DESCRIPTION

Screening and Identification of Microbial Strains

Actinobacteria were isolated from eleven soil samples collected from Wuxi and Kunming in China. The samples were diluted and plated on agar plates with 2,4-dinitrophenylhydrazine. The plates were incubated at 28° C. for 3-5 days. Colonies with red or orange transparent circle were selected for second round screening. The selected cells were cultured in liquid fermentation medium for two to five days, after which cells in 5 ml fermentation liquid were collected by centrifugation. Wet cells were added to substrate solution containing 5 g/L ferulic acid and incubated at 37° C. for 24-48 hours to convert ferulic acid into vanillin. The conversion products were further analyzed by silica gel chromatography (benzene:Hexane:chloroform:ether:acetic acid=4:3:2:1:0.1, v/v). The strain zhp06 was found to accumulate significant amount of vanillin.

Genomic DNA of strain zhp06 was extracted and its 16S rRNA sequence was found to have 98-99% similarity to those of many known *Amycolatopsis* sp. strains. According to its biochemical and physiological properties and standards set in "Actinomycetes Systems" (Science Press, 2007, P363) and "Basis of Classification of Actinomycetes" (Science Press, 1977), the strain was recognized as an *Amycolatopsis* sp. Zhp06 was then deposited in China Center for Type Culture Collection on Jul. 26, 2011 with the number of CCTCC NO: M 2011265.

Prominent features of this strain includes the following: a) the cell body is filamentous, the colony color is incanus or yellow, and the spore appears ellipsoid; b) the optimal growth temperature is from 28° C. to 37° C. with the ability to grow at 50-55° C., the optimum growth pH for Zhp06 cells is pH 6-9, and the optimal growth NaCl concentration is 0-5%; c) they can make milk coagulation and gelatin liquefaction, and produce catalase, urease, and lipase. They cannot break down cellulose as the amylase activity in these cells is low; the cells cannot produce $H_2S$ or acetylmethyl-methanol; they produce very little formic acid and other acidic substances when breaking down glucose; they can produce indole.

Cell Culture and Production of Vanillin

The slant medium contains glucose agar medium, asparagine agar medium or ISP-2 medium. ("Catalog of Chinese Bacterial Strains", Chemical Industry Press, 2007)

The screening medium adds 0.5-5 g/L benzoic acid or ferulic acid to the slant medium.

The fermentation medium contains carbon source 5-15 g/L, yeast extract 1-20 g/L, $Na_2HPO_4.10H_2O$ 1-10 g/L, $KH_2PO_4$ 0.1-2 g/L, NaCl 0.1-0.5 g/L, $MgSO_4.7H_2O$ 0.2-0.5 g/L, $CaCl_2.2H_2O$ 0.01-0.1 g/L, ferulic acid 0.05-0.5 g/L, (use NaOH to adjust the pH to 7.2-7.4). The above medium was sterilized at 121° C. for 20 minutes.

The carbon source in fermentation medium is selected from glucose, starch, sucrose, fructose and maltose.

After *Amycolatopsis* sp. zhp06 was cultivated on the agar slant at 28-37° C. for 3-6 days, the spores were suspended in sterile water and added to the fermentation medium at the ratio of 2%-5% (v/v). Cells were harvested by centrifugation (3000-6000 g, 10-15 min) after cultivation at 28-40° C., 180-220 rpm for 22-40 hours.

As a biocatalyst, the wet zhp06 cells or immobilized zhp06 cells were added to the substrate solution at the ratio from 1:2 to 1:20 (weight/volume) to form a biotransformation solution. The substrate solution contains 3-40 g/L ferulic acid, 1-10 g/L $Na_2HPO_4.10H_2O$, 0.1-0.5 g/L $KH_2PO_4$, pH 7.5-7.9. The biotransformation reaction was performed at 28-45° C. for 20-70 hours.

The immobilized cells were prepared by using carrageenan, chitosan or calcium alginate as the immobilization carrier (<<Immobilization of Enzyme and Cell>>, Chemical Industry Press, 2006).

Purification of Product

After 5-12 hours of biotransformation reaction, macroporous resin HZ-16 or HZ-802 was added into the biotransformation solution at a ratio of 5% to 50% (weight (g)/volume (ml)). When the reaction was over, the macroporous resin was filtered out and eluted at 35-40° C. with acetic ether or alcohol (two times the wet volume of macroporous resin). The eluted solution was dried by anhydrous sodium sulfate for 12-15 hours, and was filtered to remove sodium sulfate. The filtered solution was concentrated under vacuum evaporation to achieve 200-230 g/L vanillin. The concentrated vanillin solution was then left at 4° C. for vanillin crystallization.

Product Analysis and Quantification

Vanillin in biotransformation samples were extracted with butyl acetate (analytic grade) and analyzed by HPLC. (Determination of Vanillin, Eugenol and Isoeugenol by RP-HPLC. Chromatographia 60:709-713)

This invention provides an *Amycolatopsis* sp. strain (zhp06) with the ability to convert high concentrations of ferulic acid to vanillin. It also provides a method for vanillin production using the whole zhp06 and its mutant cells as a biocatalyst. The bacteria cells are first cultured under standard culture conditions. The cells are then harvested and used as a biocatalyst to convert high concentrations of ferulic acid substrate into vanillin. One advantage of the method is that the biocatalyst, the *Amycolatopsis* sp. zhp06 cells can be used repeatedly. The reaction condition of the method is very mild, leading to very little environmental pollution. Another advantage is that the production cycle of this method is short, and the purity of conversion product is very high, making it easy to be purified. This method has great potential for industrial applications.

Bio-Sample Storage:

*Amycolatopsis* sp. zhp06 was deposited in China Center for Type Culture Collection on Jul. 26, 2011 with the number of CCTCC NO: M 2011265.

EXAMPLES

Example 1

Isolation and Characterization of zhp 06 Strain

Soil samples were taken from Wuxi and Kunming in China. The samples were diluted and plated onto agar plates with 2,4-dinitrophenylhydrazine. The plates were incubated at 28° C. for 3-5 days and colonies with red or orange transparent circle were selected. Furthermore it was screened by the method of silica gel chromatography (benzene:Hexane:chloroform:ether:acetic acid=4:3:2:1:0.1). The strain zhp06 was selected for its ability to produce high amounts of vanillin.

Genomic DNA of the strain zhp06 was extracted using a bacterial DNA extraction kit (Shanghai Generay Biotech Company, Shanghai, China). The 16S rRNA gene of zhp06 was amplified by PCR using the universal bacterial RNA primers (upstream primer ACGGTTACCTTGTTACGACTT (SEQ ID NO. 1), downstream primer AGAGTTTGATCCTGGCTCAG (SEQ ID NO. 2)). Sequencing of the 16S rRNA sequences was performed by Shanghai Sangon Co., Ltd. and the sequences were submitted to GenBank with a registration number of JF828149. NCBI-BLAST was used to search for sequence homology with other 16S rRNA sequences in GenBank (see the result in Table 1). The physiological and biochemical properties of zhp06 strain was characterized as described in "Actinomycete Systematics". A salient feature of the strain is that it possesses high tolerance to changes in pH, temperature, and NaCl concentrations. *Amycolatopsis eurytherma* strain NT202 and *Amycolatopsis thermoflava* strain 173573 are two bacteria strains that have the highest sequence homology with zhp 06 strain. They are similar to each other in terms of their tolerance to changes in growth temperature and NaCl concentrations. But they use different carbon sources (e.g. arabinose, cellobiose, xylose, etc.). The zhp06 strain shares the same property with *Amycolatopsis eurytherma* strain NT202 in terms of gelatin digestion, and production of enzymes such as amylase, nitrate reductase, and urease. Therefore, zhp06 strain is considered to be an *Amycolatopsis* sp. The strain was deposited into China Center for Type Culture Collection on Jul. 26, 2011 with the number of CCTCC NO: M 2011265.

TABLE 1

16S rRNA Sequence Homology Analysis

| Strain Name | NCBI NO. | Homology |
|---|---|---|
| *Amycolatopsis thermoflava* strain 173573 | EU570741.1 | 99% |
| *Amycolatopsis* sp. ATCC 39116 | AM263203.1 | 99% |
| *Amycolatopsis eurytherma* strain NT202 | NR_036887.1 | 98% |
| *Amycolatopsis thermoflava* strain N1165 | NR_024890.1 | 98% |
| *Amycolatopsis methanolica* | AJ249135.1 | 98% |
| *Amycolatopsis thermoflava* strain N1165 | NR_024890.1 | 98% |
| *Amycolatopsis methanolica* partial | X54274.1 | 97% |
| *Amycolatopsis albidoflavus* | AB327251.1 | 95% |
| *Amycolatopsis taiwanensis* | AB327255.1 | 94% |
| *Amycolatopsis orientalis* IFO 12806$^T$ | AJ400711 | 92% |
| *Streptomyces eurythermus* | D63870 | 90% |
| *Amycolatopsis mediterranei* DSM 13685$^T$ | X76957 | 90% |
| *Streptomyces setonii* NBRC 13085 | AB184300.1 | 89% |
| *Pseudonocardia thermophila* ATCC 19285T | X53195 | 86% |
| *Bacillus subtilis* subsp | AL009126.3 | 77% |
| *Bacillus fusiformis* | AM062692.1 | 73% |

TABLE 2

Biochemical and physiological properties of *Amycolatopsis* sp. zhp06

| Characteristic | zhp06 | 1 | 2 |
|---|---|---|---|
| Aerial mycelium | + | + | + |
| Color of aerial mycelium | white | white | white |
| Utilization of: | | | |
| L-(+)-Arabinose | w | + | + |
| D(+)-Cellobiose | w | + | + |
| Dextrin/dextran | w | + | − |
| D-(+)-Fructose | + | + | + |
| D-(+)-Glactose | w | + | + |

TABLE 2-continued

Biochemical and physiological properties of *Amycolatopsis* sp. zhp06

| Characteristic | zhp06 | 1 | 2 |
|---|---|---|---|
| meso-ino-sitol | − | + | − |
| D-(+)-lactose | w | w | + |
| D-(+)-maltose | w | − | − |
| D-(+)-Mannitol | w | + | + |
| D-(+)-Melezitose | − | o | − |
| D-(−)-Sorbitol | − | + | + |
| sucrose | − | − | − |
| D-(+)-Trehalose | − | + | + |
| D-(+)-Xylose | w | + | + |
| Hydrolysis of: | | | |
| Gelatin | + | + | − |
| Growth | | | |
| Growth at 10° C. | − | − | − |
| Growth at 45° C. | + | + | + |
| NaCL(5%) | + | + | + |
| Product | | | o |
| Amylase | − | − | |
| Nitrate reductase | + | + | |
| Urease | + | + | |

1, stands for *Amycolatopsis eurytherma* strain NT202;
2, stands for *Amycolatopsis thermoflava* strain 173573;
+, means positive;
w, means slightly positive;
−, means negative.

Example 2

Use Different Carbon Sources for Culturing *Amycolatopsis* sp. zhp06 Cells

The spore of *Amycolatopsis* sp. zhp06 was inoculated to fermentation medium with different carbon sources selected from maltose, fructose, glucose, soluble starch or sucrose. The zhp06 cells grew at 35° C., 180 rpm for 24 hours. 20 mL fermentation broth was centrifuged at the speed of 5000 rpm for 10 minutes, and the cells were collected. The cells were added into substrate solution with 12 g/L ferulic acid. The biotransformation reaction was performed at 35° C., 180 rpm for 48 hours.

The fermentation medium contained 5 g/L carbon source, 10 g/L yeast powder, 5 g/L $Na_2HPO_4.10H_2O$, 0.5 g/L $KH_2PO_4$, 0.2 g/L NaCl, 0.2 g/L $MgSO_4.7H_2O$, 0.1 g/L $CaCl_2.2H_2O$, 0.1 g/L ferulic acid (pH 7.4). The above medium was sterilized at 121° C. for 20 min. Carbon source mentioned above was selected from maltose, fructose, glucose, soluble starch and sucrose. The production of vanillin and other related compounds by zhp06 cells cultured in different carbon sources was compared and shown in table 3.

TABLE 3

Products of *Amycolatopsis* sp. zhp06 utilizing different carbon sources

| Carbon source | Ferulic acid (g/L) | Vanillic acid (g/L) | Guaiacol (g/L) | Vanillin (g/L) | Vanillyl alcohol (g/L) | Yield of vanillin (%) |
|---|---|---|---|---|---|---|
| maltose | 1.49 | 0.82 | 0.55 | 5.08 | 0.40 | 54.1 |
| fructose | 2.02 | 0.39 | 0.25 | 5.48 | 0.66 | 58.3 |
| glucose | 1.91 | 0.64 | 0.27 | 4.96 | 0.64 | 52.7 |
| Soluble starch | 1.34 | 0.90 | 0.33 | 5.31 | 0.63 | 56.5 |
| Sucrose | 1.56 | 0.73 | 0.29 | 5.06 | 0.51 | 53.8 |

Example 3

Repeated Use of Biocatalyst Cells

The cultivation method was as Example 2 with glucose as the carbon source, 100 ml fermentation broth was centrifuged for 10 minutes at the speed of 5000 rpm, and then the cells were collected. 3.5 g cells were added into 20 ml substrate solution with 16 g/L ferulic acid. The biotransformation reaction was performed at 35° C., 180 rpm, for 24 hours. After biotransformation, the cells were recycled and added into another 20 mL substrate solution with 16 g/L ferulic acid again. The cells were repeatedly used for 7 times and the results were shown in Table 4.

TABLE 4

Analysis for products generated by recycled cells

| Repeat times | Vanillyl alcohol (g/L) | Vanillin (g/L) | Vanillic acid (g/L) | Guaiacol (g/L) | Ferulic acid (g/L) | Yield of Vanillin (%) |
|---|---|---|---|---|---|---|
| 1 | 0.34 | 3.51 | 0.76 | 0.56 | 5.6 | 28 |
| 2 | 0.55 | 3.82 | 3.64 | 1.58 | 0.04 | 30 |
| 3 | 0.94 | 7.97 | 1.81 | 0.46 | 0.14 | 64 |
| 4 | 0.95 | 7.41 | 1.30 | 0.40 | 0.36 | 59 |
| 5 | 0.79 | 8.02 | 1.40 | 0.24 | 0.76 | 64 |
| 6 | 0.87 | 8.21 | 1.85 | 0.09 | 0.23 | 65 |
| 7 | 1.39 | 7.93 | 3.25 | 0.15 | 1.17 | 63 |

Example 4

Process of Making Immobilized Cells

The immobilized cells were obtained by the following method:
1) 5 g cells were obtained by the method as described in example 2;
2) The cells in step 1) were suspended in the same volume of saline and mixed with 5.4% carrageenan solution at the ratio of 1:2 (v/v) at 58° C.;
3) The mixture in step 2) was immersed in 0.3M cold potassium chloride solution and reacted at 10° C. for 4 hours.

10 g immobilized cells were added into substrate solution with 16 g/L ferulic acid. The biotransformation reaction was performed at 37° C. for 24 hours. The concentration of vanillin was measured and the immobilized cells were recycled.

The above steps were conducted repeatedly for 3 times, and the concentration of vanillin achieved was 5.6 g/L, 5.3 g/L, 4.4 g/L, respectively.

Example 5

Biotransformation Reaction with Different Substrate Concentrations 5 g cells (obtained from example 2 using starch as the carbon source) were added into 20 ml substrate solution with 20, 30, and 40 g/l ferulic acid. The biotransformation was performed at 35° C., 180 rpm for 12 hours. 2 g macroporous resin HZ-16 was then added to the biotransformation solution, and was incubated at 35° C. for another 48 hours. Production of vanillin was shown in Table 5.

TABLE 5

Effect of substrate concentrations on production of vanillin

| substrate concentration (g/L) | Vanillyl alcohol (g/L) | Vanillin (g/L) | Vanillic acid (g/L) | Guaiacol (g/L) | Ferulic acid (g/L) |
|---|---|---|---|---|---|
| 20 | 0.61 | 7.88 | 0.03 | 6.46 | 0.46 |
| 30 | 0.19 | 10.03 | 0.06 | 5.51 | 0.65 |
| 40 | 0.46 | 10.08 | 2.16 | 4.52 | |

Example 6

Purification of Vanillin

The purification method comprises the following steps:
1) 1L biotransformation solution containing 5.34 g/L Vanillin were added to 300 g macroporous resin HZ-16. After 3 hours of absorption, macroporous resin HZ-16 were filtered out and eluted twice with 600 ml acetic ether at 35° C., each time for 2 hours.
2) The acetic ether elute (~1200 ml) was dried by anhydrous sodium sulfate for 12-15 hours and was vacuum evaporated until vanillin concentration reaching 22%.
3) The solution obtained from step 2 was settled at 4° C. for crystallization.
4) 3.66 g vanillin was obtained with purity of 95%.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for vanillin production using cells of *Amycolatopsis* sp. strain (zhp06) or its mutant strains, comprising the steps of:
   (a) addition of *Amycolatopsis* sp. zhp06 cells isolated from a standard cell culture to a substrate solution comprising about 3-40 g/L ferulic acid to form a biotransformation solution, whereby the ferulic acid is converted to vanillin using said *Amycolatopsis* sp. zhp06 cells as a biocatalyst; and
   (b) purification of vanillin from said biotransformation solution after 5-12 hours of said conversion reaction of ferulic acid to vanillin, wherein said purification is performed by adding 5-50% (w/v) of macroporous absorbent resin to said biotransformation solution, wherein vanillin is extracted from the solution using said absorbent resin which is then eluted with acetic ether or alcohol at 35-40° C. to produce an eluate solution containing vanillin; and wherein said eluate solution is dried by anhydrous sodium sulfate and further dried by vacuum evaporation to produce a concentrated extract containing 200-230 g/L of vanillin; and subsequently, said concentrated extract is settled at 4° C. for vanillin crystallization thereby purifying vanillin from the biotransformation solution.

2. The method according to claim 1, wherein the standard cell culture comprises a fermentation medium containing 5-15 g/L carbon source, 1-20 g/L yeast powder, 1-10 g/L $Na_2HPO_4 \cdot 10H_2O$, 0.1-2 g/L $KH_2PO_4$, 0.1-0.5 g/L NaCl, 0.2-0.5 g/L $MgSO_4 \cdot 7H_2O$, 0.01-0.1 g/L $CaCl_2 \cdot 2H_2O$, 0.05-0.5 g/L ferulic acid, and wherein said fermentation medium is sterilized at 121° C. for 20 min.

3. The method according to claim 2, wherein the carbon source is selected from glucose, starch, sucrose, fructose and maltose.

4. The method according to claim 1, wherein said substrate solution contains 3-40 g/L ferulic acid, 1-10 g/L $Na_2HPO_4 \cdot 10H_2O$, 0.1-0.5 g/L $KH_2PO_4$ (pH 7.5), and wherein said conversion of ferulic acid to vanillin was performed at 28-45° C. for 20-70 hours.

5. The method according to claim 1, wherein a weight-to-volume ratio (w/v) of the wet weight (g) of said *Amycolatopsis* sp. zhp06 cells and the volume (ml) of said substrate solution is from 1:2 to 1:20.

6. The method according to claim 1, further comprising recycling said *Amycolatopsis* sp. zhp06 cells from the biotransformation solution and adding said cells into a fresh biotransformation solution comprising ferulic acid for another vanillin production.

7. The method according to claim 1, wherein said *Amycolatopsis* sp. zhp06 cells were isolated from the standard cell culture by centrifugation.

8. The method of claim 1, wherein the macroporous absorbent resin is HZ-16 or HZ-802.

9. The method of claim 1, wherein said eluate solution is dried by anhydrous sodium sulfate for 12-15 hours.

\* \* \* \* \*

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Universal DNA primer for bacterial 16S RNA

<400> SEQUENCE: 1
acggttacct tgttacgact t                                          21

<210> SEQ ID NO 2
<211> LENGTH: 20

```
<212> TYPE: DNA
<213> ORGANISM: Artificial Sequence
<220> FEATURE:
<223> OTHER INFORMATION: Universal DNA primer for bacterial 16S RNA

<400> SEQUENCE: 2
agagtttgat cctggctcag                                        20
```